(12) United States Patent
Kloog et al.

(10) Patent No.: US 8,232,253 B2
(45) Date of Patent: Jul. 31, 2012

(54) TREATMENT OF LUNG CANCER

(75) Inventors: Yoel Kloog, Herzliya (IL); Adi Zundelevich, Kiryat Ono (IL); Roni Haklai, Ramat Gan (IL)

(73) Assignee: Ramot at Tel-Aviv University Ltd. (IL)

( * ) Notice: Subject to any disclaimer, the term of this patent is extended or adjusted under 35 U.S.C. 154(b) by 0 days.

(21) Appl. No.: 12/519,578

(22) PCT Filed: Dec. 17, 2007

(86) PCT No.: PCT/IL2007/001556
§ 371 (c)(1),
(2), (4) Date: Nov. 13, 2009

(87) PCT Pub. No.: WO2008/075342
PCT Pub. Date: Jun. 26, 2008

(65) Prior Publication Data
US 2010/0136138 A1    Jun. 3, 2010

Related U.S. Application Data

(60) Provisional application No. 60/875,915, filed on Dec. 19, 2006.

(51) Int. Cl.
*A01N 37/10* (2006.01)
*A01N 43/02* (2006.01)
*A61K 31/19* (2006.01)
*A61K 31/335* (2006.01)

(52) U.S. Cl. ............................ 514/34; 514/449; 514/569
(58) Field of Classification Search .................. None
See application file for complete search history.

(56) References Cited

U.S. PATENT DOCUMENTS

2004/0072258 A1 * 4/2004 Kloog et al. .................. 435/7.2

FOREIGN PATENT DOCUMENTS

| WO | 95/13059 A1 | 5/1995 |
| WO | 2006/023639 A1 | 3/2006 |
| WO | 2007/064448 | 6/2007 |

OTHER PUBLICATIONS

Dorwald (Side Reactions in Organci Synthesis: A guide to successful synthesis design, Weinheim: WILEY-VCH, Verlag GmbH & co. KGaA, 2005, Preface.*
Hirose et al. Phase I study of the combination of gemcitabine and nedaplatin for treatment of previously untreated advanced non-small cell lung cancer. Lung Cancer, 39, 2003, 91-97.*
Sandler et al. Phase III trial of gemcitabine plus cisplatin verus cisplatin alone in patients with locally advanced or metastatic non-small cell lung cancer. Journal of Clinical Oncology, vol. 18, No. 1, Jan. 2000, pp. 122-130.*
Berenbaum et al. What is synergy? Pharmacological Reviews, 1989.*
Gana-Weisz Mali et al: "The Ras inhibitor S-trans, Trans-farnesylicylicacid Chemosensitizes Human Tumor Cells without Causing Resistance" Clinical Cancer Research, The American Association for Cancer Research, US, vol. 8, No. 2, 2002, pp. 555-565.
Beiner M E et al: "Ras Antagonist Inhibits Growth and Chemosensiuzes Human Epitheliaf Ovarian Cancer Cells" International Journal of Gynecological Cancer, Blackwell Scientific Publicattons, Cambridge, MA, US, vol. 16, No. suppl 1, Jan. 2006, pp. 200-206.
International Search Report, PCT/IL2007/001556, dated May 2, 2008.
Blum, Roy et al, "Ras inhibition in glioblastoma down-regulates hypoxi a-inducible factor-laipha, causing glycolysis shutdown and cell death." Cancer Research, Feb. 1, 2005, vol. 65, No. 3, pp. 999-1006.
Zundelevich, Adi et al, "Suppression of lung cancer tumor growth in a nude mouse model by the Ras inhibitor salirasib (farnesylhiosalicylic acid)." Molecular Cancer Therapeutics Jun. 2007, vol. 6, No. 6, Jun. 2007 , pp. 1765-1773.

* cited by examiner

*Primary Examiner* — Brandon Fetterolf
*Assistant Examiner* — Anna Pagonakis
(74) *Attorney, Agent, or Firm* — Lerner, David, Littenberg, Krumholz & Mentlik, LLP

(57) ABSTRACT

Disclosed are methods of treating lung cancer by administering to a human in need thereof effective amounts of FTS, or various analogs thereof, or a pharmaceutically acceptable salt thereof, optionally, in combination with a chemotherapeutic agent. Chemotherapeutic agents, and combinations thereof, for use with FTS, its analogs, or its salts are also disclosed.

5 Claims, 10 Drawing Sheets

INCUBATION OF THE CELLS WITH 75μM FTS FOR 48 h
INHIBITED INCORPORATION OF BrdU INTO THE DNA OF A549 CELLS

PHOTOMICROGRAPH IMAGES (72 h) OF CONTROL (LEFT) AND FTS-TREATED CELLS (RIGHT)
REVEAL THAT FTS (75μM) REDUCES THE OVERALL NUMBER OF HUMAN LUNG CANCER A549 CELLS

FTS (μM) INHIBITS GROWTH OF A549 CELLS

FACS ANALYSIS RESULTS DEMONSTRATE FTS INDUCED CELL-CYCLE ARREST IN A549 CELLS

FTS (μM) INHIBITS GROWTH OF H-1299 CELLS

FTS (μM) INHIBITS GROWTH OF SK-MES-1 CELLS

FTS (μM) INHIBITS GROWTH OF H23 CELLS

FTS (μM) INHIBITS GROWTH OF HTB54 CELLS

| CELL LINE | RAS MUTATION | $IC_{50}$ (µM) |
|---|---|---|
| A549 | K-RAS | 40 |
| H23 | K-RAS | 75 |
| HTB54 | K-RAS | 30 |
| H1299 | NONE | 30 |
| SK-MES-1 (HTB58) | NONE | 50 |

SUMMARY OF LUNG CANCER GROWTH INHIBITION BY FTS

FTS INDUCES STRESS FIBER (F-ACTIN) AND FOCAL ADHESION (α-VINCULIN) FORMATION IN A549 CELLS AS ILLUSTRATED BY FLUORESCENCE MICROSCOPY

FTS INHIBITS THE ANCHORAGE-DEPENDENT GROWTH OF A549 CELLS IN SOFT AGAR

EFFECTS OF COMBINATION OF FTS AND GEMCITABINE ON THE NUMBER OF A549 CELLS

EFFECTS OF COMBINATION OF FTS AND DOXORUBICINE ON THE NUMBER OF A549 CELLS

EFFECTS OF COMBINATION OF FTS AND CISPLATIN ON THE NUMBER OF A549 CELLS

EFFECTS OF COMBINATION OF FTS AND PACLITAXEL ON THE NUMBER OF A549 CELLS

A549 (i.p. FTS)
EFFECTS OF FTS (i.p.) IN A549 CELL LUNG CANCER NUDE MOUSE MODELS

HTB-58 (i.p. FTS)
EFFECTS OF FTS (i.p.) IN HTB-58 CELL LUNG CANCER NUDE MOUSE MODELS

A549 (ORAL FTS)
EFFECTS OF FTS (ORAL) IN A549 CELL LUNG CANCER NUDE MOUSE MODELS

A549 (ORAL FTS/i.p. GEMCITABINE)
EFFECTS OF FTS, ALONE, AND IN COMBINATION WITH GEMCITABINE IN LUNG CANCER NUDE MOUSE MODELS

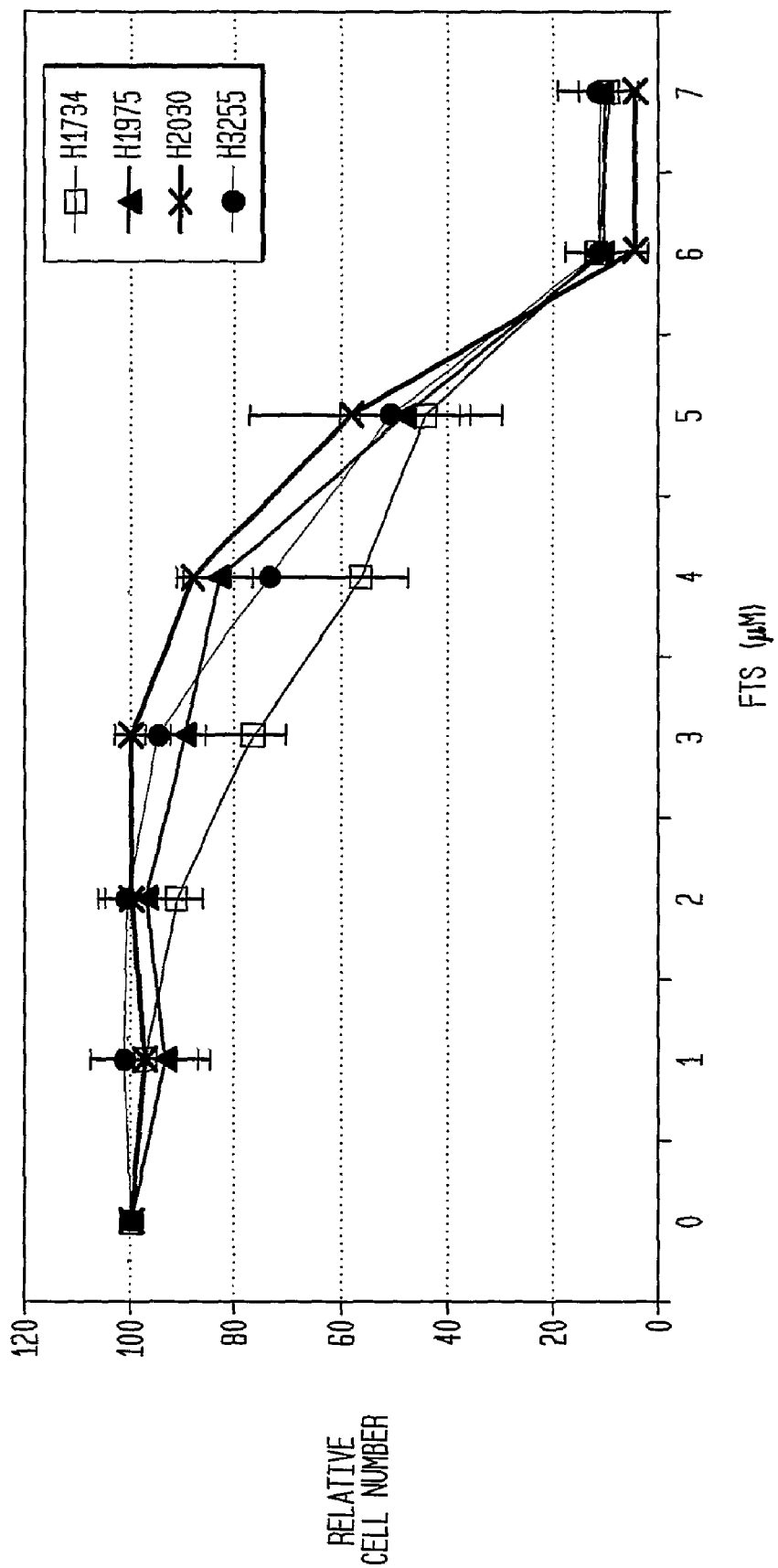

TREATMENT OF LUNG CANCER

CROSS-REFERENCE TO RELATED APPLICATIONS

This application claims the benefit of the filing date of U.S. Provisional Patent Application No. 60/875,915 filed Dec. 19, 2006, the disclosure of which is hereby incorporated herein by reference.

BACKGROUND OF THE INVENTION

Lung cancer is the leading cause of cancer-related deaths in the world [Greenlee et al., CA Cancer J Clin 51:15-36 (2001)]. Only one in ten patients diagnosed with this disease will survive the next five years. Although lung cancer was previously an illness that affected predominately men, the lung cancer rate for women has been increasing in the last few decades, which has been attributed to the rising ratio of female to male smokers. More women die of lung cancer than any other cancer, including breast cancer, ovarian cancer and uterine cancers combined. [American Cancer Society. *Cancer Facts and Figures*. 2006. Atlanta: American Cancer Society (2006)]. Despite advances in surgery, chemotherapy, and radiation therapy, survival rates have barely changed in the last decade, and long-term survival remains dramatically poor.

Lung cancers can arise in any part of the lung. Ninety to 95% of cancers of the lung are thought to arise from the epithelial, or lining cells of the larger and smaller airways (bronchi and bronchioles); for this reason lung cancers are sometimes called bronchogenic carcinomas. Cancers can also arise from the pleura (the thin layer of tissue that surrounds the lungs), called mesotheliomas, or rarely from supporting tissues within the lungs, for example, blood vessels.

It has been established that lung cancer arises as a consequence of the accumulation of multiple genetic changes involving critical genes controlling cell motility, proliferation, differentiation, and apoptosis. [Sekido at al., *Biochimica et Biophysica Acta* 1378:F21-F59 (1998)].

According to the American Cancer Society, there are two major types of lung cancer: small cell lung cancer (SCLC) and non-small cell lung cancer (NSCLC). SCLC comprises about 15% of all cancers. NSCLC, however, comprises about 85% of all lung cancers and is divided into three distinct sub-types: squamous cell carcinoma (about 25-30% of the cases), large cell carcinomas (about 10-15%), and adenocarcinomas (about 40%). The cells in these sub-types differ in size, shape, and chemical make-up. These lung cancers are inclusive of bronchogenic carcinoma, bronchial carcinoids, chondromatous hamartoma, solitary pulmonary nodules, pulmonary sarcomas, undifferentiated small cell carcinoma, undifferentiated large cell carcinoma, and bronchioloalveolar carcinomas.

Current research indicates that the factor with the greatest impact on risk of lung cancer is long-term exposure to inhaled carcinogens. The most common means of such exposure is tobacco smoke.

Treatment and prognosis depend upon the histological type of cancer and the stage (degree of spread). Possible treatment modalities include surgery, chemotherapy, and/or radiotherapy.

SUMMARY OF THE INVENTION

A first aspect of the present invention is directed to a method of treating lung cancer. The method comprises administering to a human in need thereof an effective amount of S-farnesylthiosalicylic acid (FTS) or an analog thereof, or a pharmaceutically acceptable salt thereof.

Another aspect of the present invention is directed to a method of treating lung cancer. The method comprises administering to a human in need thereof effective amounts of S-farnesylthiosalicylic acid (FTS) or an analog thereof, or a pharmaceutically acceptable salt thereof, and a chemotherapeutic agent.

The results of a first set of experiments described herein showed that in five human cell lines commonly used in the study of lung cancer [non-small cell lung carcinoma cell lines (NSCLC), a human lung squamous cell carcinoma cell line, and a lung epidermoid carcinoma cell line)], FTS inhibited cancer cell growth.

The results of a further set of experiments described herein showed that in a human lung carcinoma A549 cell line, FTS reversed the transformed morphology of the cells, altered the cytoskeletal organization of the cells, and inhibited the anchorage-independent growth of cancer cell colonies.

The results of another set of experiments described herein showed that the combined treatment of FTS with a chemotherapeutic agent in vitro caused greater cell death with both drugs than treatment with either drug alone in a human lung epithelial carcinoma A549 cell line.

The results of an additional set of experiments described herein showed that administering FTS i.p. to a lung cancer cell nude mouse model inhibited A549 and HTB-58 (SK-MES-1) tumor cell growth.

Yet another set of experiments described herein showed that the combination of FTS with a chemotherapeutic agent in vivo caused greater cell death with the combined treatment than with either drug alone in a nude mouse model.

The results of another set of experiments described herein showed that in four human lung cancer (NSCLC) cell lines (H1734, H2030, H1975, and H3255) FTS sensitized the cells resulting in cell death.

DESCRIPTION OF THE DRAWINGS

FIG. 15 is a graph illustrating the effects of increasing concentrations of FTS on human NSCLC cell lines H1734 and H2030 (KRAS mutations) and H1975 and H3255 (EGFR mutations).

DETAILED DESCRIPTION

Figure 1:
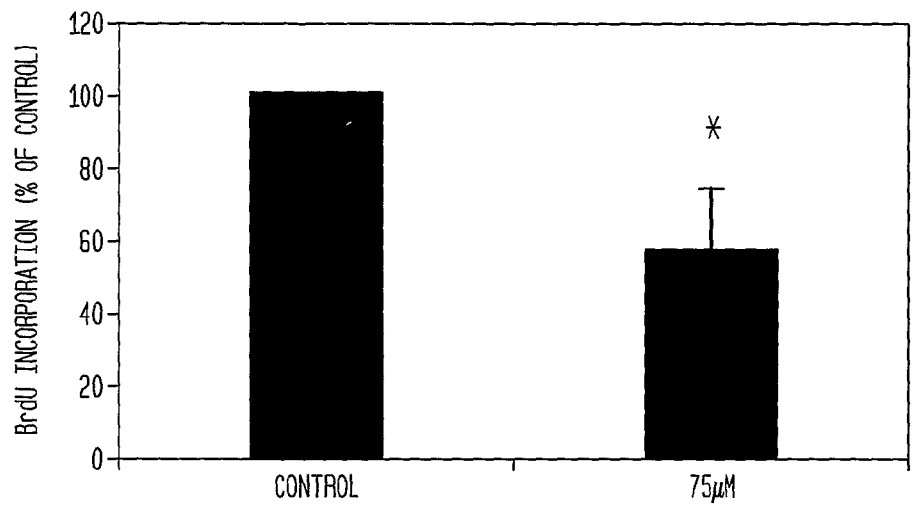
FIG. 1 is a bar graph illustrating the inhibition of BrdU into the DNA of A549 cells (NSCLC) after incubation of the FTS-treated cells (75 µM) for 48 h, expressed as a percentage of control.

Ras proteins act as on-off switches that regulate signal-transduction pathways controlling cell growth, differentiation, and survival. [Reuther, G. W., Der, C. J., Curr Opin Cell Biol 12:157-65 (2000)]. They are anchored to the inner leaflet of the plasma membrane, where activation of cell-surface receptors, such as receptor tyrosine kinase, induces the exchange of guanosine diphosphate (GDP) for guanosine triphosphate (GTP) on Ras and the conversion of inactive Ras-GDP to active Ras-GTP. [Scheffzek, K., Ahmadian, M. R., Kabsch, W., et al. Science 277:333-7 (1997)]. The active Ras protein promotes oncogenesis through activation of multiple Ras effectors that contribute to deregulated cell growth, differentiation, and increased survival, migration and invasion. [See, e.g., Downward, J., Nat. Rev. Cancer 3:11-22 (2003); Shields, J. M., et al., Trends Cell Biol 10:147-541 (2000); and Mitin, N., et al., Curr Biol 15:R563-74 (2005)].

FTS is a potent Ras inhibitor that acts in a rather specific manner on the active, GTP-bound forms of H-, N-, and K-Ras proteins. [Weisz, B., Giehl, K., Gana-Weisz, M., Egozi, Y., Ben-Baruch, G., Marciano, D., Gierschik, P., Kloog, Y., Oncogene 18:2579-2588 (1999); Gana-Weisz, M., Halaschek-Wiener, J., Jansen, B., Elad, G., Haklai, R., Kloog, Y., Clin. Cancer Res. 8:555-65 (2002)]. FTS competes with Ras-GTP for binding to specific saturable binding sites in the plasma membrane, resulting in mislocalization of active Ras and facilitating Ras degradation. [Haklai, et al., Biochemistry 37(5):1306-14 (1998)]. This competitive inhibition prevents active Ras from interacting with its prominent downstream effectors and results in reversal of the transformed phenotype in transformed cells that harbor activated Ras. As a consequence, Ras-dependent cell growth and transforming activities, both in vitro and in vivo, are strongly inhibited by FTS. [Weisz, B., et al., supra.; Gana-Weisz, M., et al., supra.].

FTS and its analogs useful in the present invention are represented by formula I:

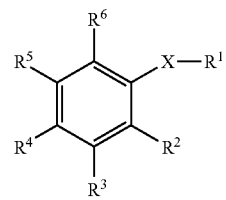

wherein $R^1$ represents farnesyl, geranyl or geranyl-geranyl;

$R^2$ is $COOR^7$, or $CONR^7R^8$, wherein $R^7$ and $R^8$ are each independently hydrogen, alkyl or alkenyl;

$R^3$, $R^4$, $R^5$ and $R^6$ are each independently hydrogen, alkyl, alkenyl, alkoxy, halo, trifluoromethyl, trifluoromethoxy, or alkylmercapto; and X represents S.

The structure of FTS is as follows:

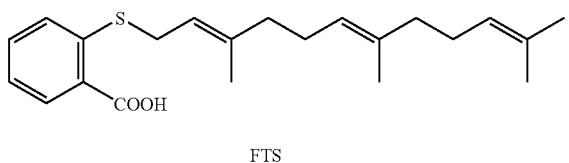

FTS

FTS analogs embraced by formula I, and which may be suitable for use in the present invention, include 5-fluoro-FTS, 5-chloro-FTS, 4-chloro-FTS, S-farnesyl-thiosalicylic acid methyl ester (FTSME), and S-geranyl, geranyl-thiosalicylic acid (GGTS). Structures of these compounds are set forth below.

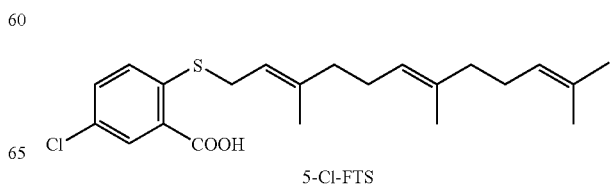

5-Cl-FTS

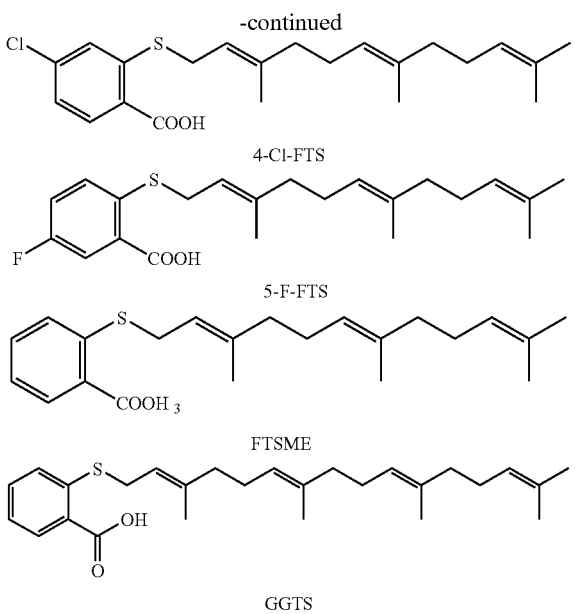

In some embodiments, GGTS is administered in an amount effective to treat a patient diagnosed with lung cancer.

Methods for preparing the compounds of formula I are disclosed in U.S. Pat. Nos. 5,705,528 (RE39,682) and 6,462,086. See also, Marom, M., Haklai, R., Ben-Baruch, G., Marciano, D., Egozi, Y., Kloog, Y., J Biol Chem 270:22263-70 (1995).

Pharmaceutically acceptable salts of the Ras antagonists of formula I may be useful. These salts include, for example, sodium and potassium salts. Other pharmaceutically acceptable salts may be selected in accordance with standard techniques as described in Berge, S. M., Bighley, L. D., and Monkhouse, D. C., J. of Pharm. Sci. 66(1):1-19 (1977). In preferred embodiments, however, FTS and its analogs are not administered in the form of a salt (i.e., they are administered in non-salified form).

In some embodiments, treatment also includes administering an anti-cancer therapy which includes, for example, chemotherapy, radiation therapy, immunotherapy or gene therapy, and combinations thereof.

In some embodiments, treatment includes administering a chemotherapeutic agent to a patient diagnosed with lung cancer. Chemotherapeutic agents are those medications that are used to treat various forms of cancer and, particularly, lung cancer and its various forms and associated manifestations. Generally, these medications are given in a particular regimen over a period of weeks. In some cases, combination chemotherapy may be recommended. Methods of preparing and using chemotherapeutic agents are well-known in the art. See, e.g., *Remington: The Science and Practice of Pharmacy* (21st Edition), Lippincott, Williams & Wilkins, (2005).

Chemotherapeutic agents may be administered as the first line of treatment or it may be started after a tumor is surgically resected, for example. The agents may be administered by various methods including, oral (by mouth), injection (intramuscular or subcutaneous), intravenous (IV), intra-arterial (into the arteries, intralesional (directly into the tumor), intraperitoneal (into the peritoneal cavity), intrathecal (into the spinal fluid), and topical (applied to the skin). A variety of factors, including the overall health, size and weight of the patient, the patient's tolerance to the treatment, and the type and stage of the cancer, will determine the type of chemotherapy used and the mode and duration of administration. Optimally, dosages for each of the chemotherapeutic agents are prescribed in accordance with current labeling instructions. Dosages, however, may be adjusted to satisfy a patient's needs.

Examples of chemotherapeutic agents include, but are not limited to, paclitaxel (Taxol®), docetaxel (Taxotere®), cisplatin, carboplatin (Paraplatin®), gemcitabine hydrochloride (Gemzar®), doxorubicin hydrochloride, etoposide (Etopophos®, Vepesid®), pemetrexed (Alimta®), topotecan (Hycamtin®), vinblastine (Velbe®), Vindesine (Eldisine®), vinorelbine (Navelbine®), ifosfamide (Mitoxana®), and Mitomycin. Those most commonly used agents to treat lung cancer include: gemcitabine, cisplatin, carboplatin, vinorelbine, paclitaxel, docetaxel, and doxorubicin. These agents may be given in combination, for example, vinorelbine and cisplatin or carboplatin; gemcitabine with cisplatin or carboplatin or paclitaxel; MIC (mitomycin, ifosfamide and cisplatin); MVP (mitomycin, vinblastine and cisplatin); and EC (etoposide and carboplatin).

In some embodiments, the chemotherapeutic agent is paclitaxel (Taxol®) [5,20-Epoxy-1,2,4,7,10,13-hexahydroxytax-11-en-9-one 4,10-diacetate 2-benzoate 13-ester with (2R,3S)—N-benzoyl-3-phenylisoserine], an anti-neoplastic agent isolated from the bark of the Pacific yew tree, *Taxus brevifolia*. Paclitaxel is an antimicrotubule antineoplastic agent. Paclitaxel promotes microtubule assembly by enhancing the polymerisation of tubulin, the protein subunit of spindle microtubules, even in the absence of the mediators normally required for microtubule assembly (e.g., guanosine triphosphate (GTP)), thereby inducing the formation of stable, nonfunctional microtubules. It is a colorless to slightly yellow viscous solution.

In one example, combination chemotherapy using Taxol® and cisplatin is indicated. The recommended regimen, given every 3 weeks, is Taxol® administered intravenously over 24 hours at a dose of 135 mg/m² followed by cisplatin at 75 mg/m².

In some embodiments, the chemotherapeutic agent is docetaxel (Taxotere®) [(2R,3S)—N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate], an antineoplastic agent belonging to the taxoid family. It is prepared by semisynthesis beginning with a precursor extracted from the renewable needle biomass of yew plants. Docetaxel differs from paclitaxel at two positions in its chemical structure. It has a hydroxyl functional group on carbon 10, whereas paclitaxel has an acetate ester and a tert-butyl substitution exists on the phenylpropionate side chain. The carbon 10 functional group change causes docetaxel to be more lipid soluble than paclitaxel. [Clarke, S. J., Rivory, L. P., Clin Pharmacokinet 36(2):99-114 (1999)]. The main mode of therapeutic action of docetaxel is the suppression of microtubule dynamic assembly and disassembly. [Lyseng-Williamson, K. A., Fenton, C., Drugs 65(17):2513-31 (2005); Yvon, A. C., Wadsworth, P., Jordan, M. A., The American Society for Cell Biology 10:947-959 (1999)]. The docetaxel injection concentrate is a clear yellow to brownish-yellow viscous solution.

When used as a single agent therapy, a recommended dose regimen of docetaxel for patients is 75 mg/m² administered intravenously over 1 hour every 3 weeks.

In some embodiments, the chemotherapeutic agent is a platinum-based drug. The platinum-based drugs useful in the practice of the present invention include cisplatin [cis-diamminedichloroplatinum(II)] and its analogs, e.g., carboplatin [diammine(1,1-cyclobutanedicarboxylato)-platinum(II)].

These drugs are known to inflict damage on cellular nucleic acids, including DNA. Cisplatin acts by cross-linking DNA in various different ways, making it impossible for rapidly dividing cells to duplicate their DNA for mitosis. The damaged DNA sets off DNA repair mechanisms, which activate apoptosis when repair proves impossible. Methods of preparing and using cisplatin as an anti-cancer agent are described in, for example, U.S. Pat. No. 5,562,925 and *Inorg Synth* 7:239 (1963).

Carboplatin differs from cisplatin in that it has a closed cyclobutane dicarboxylate moiety on its leaving group in contrast to the readily leaving chloro groups. This results in very different DNA binding kinetics. Methods of preparing and using carboplatin as an anti-cancer agent are described in, for example, U.S. Pat. No. 4,657,927 and *Inorg Chem Acta* 46:L15 (1980). Both cisplatin and carboplatin are indicated for combination chemotherapy.

A recommended dosage of cisplatin for adults and children when used as single agent therapy is 50-100 mg/m$^2$ as a single IV infusion every 3-4 weeks, or 15-20 mg/m$^2$ as a daily IV infusion for 5 days every 3-4 weeks.

A recommended dosage of carboplatin in previously untreated adult patients with normal kidney function is 400 mg/m$^2$ as a single IV dose administered by short-term (15 to 60 minutes) infusion. Therapy should not be repeated until four weeks after the previous carboplatin course, and/or until the neutrophil count is at least 2000 cells/mm$^3$ and the platelet count is at least 100,000 cells/mm$^3$.

In some embodiments, the chemotherapeutic agent is gemcitabine hydrochloride (Gemzar®) [2'-deoxy-2',2'-difluorocytidine monohydrochloride]. The cytotoxic effect of gemcitabine is attributed to a combination of two actions of the diphosphate and the triphosphate nucleosides, which leads to inhibition of DNA synthesis. It is a white powder, which forms a clear solution. Gemcitabine, alone or in combination with cisplatin, is indicated for the first line treatment of patients with locally advanced or metastatic non-small cell lung cancer. [See, e.g., FDA REVISED LABEL—VERSION 082598; 010603; 051904; 042005; 042605 for Gemzar®]. Combination chemotherapy for treatment of lung cancer (NSCLC) with gemcitabine also includes carboplatin [See, e.g., Tassarini, D., et al., *Tumori* 90:54-59 (2004)] and paclitaxel [See, e.g., Kosmidis, P., J Clin Oncol. 20(17):3578-85 (2002)].

A recommended adult dose of gemcitabine (Gemzar®) as a single agent for lung cancer (NSCLC) is 1000 mg/m$^2$, given by 30-minute intravenous infusion. This should be repeated once weekly for three weeks, followed by a one-week rest period. This four-week cycle is then repeated. Dosage reduction with each cycle or within a cycle may be applied based upon the amount of toxicity experienced by the patient.

A recommended adult dose of gemcitabine for combination therapy using cisplatin, for example, has been investigated using two dosing regimens. One regimen used a three-week schedule and the other used a four-week schedule. The three-week schedule used gemcitabine 1250 mg/m$^2$, given by 30-minute intravenous infusion, on days 1 and 8 of each 21-day cycle. Cisplatin should be administered intravenously at 100 mg/m$^2$ on day 1 after the infusion of Gemzar®. Dosage reduction with each cycle or within a cycle may be applied based upon the amount of toxicity experienced by the patient.

The four-week schedule used gemcitabine 1000 mg/m$^2$, given by 30-minute intravenous infusion, on days 1, 8, and 15 of each 28-day cycle. Cisplatin at a dose of 100 mg/m$^2$ should be administered intravenously after the infusion of Gemzar® on Day 1. Dosage reduction with each cycle or within a cycle may be applied based upon the amount of toxicity experienced by the patient.

In some embodiments, the chemotherapeutic agent is doxorubicin hydrochloride. Doxorubicin [5,12-Naphthacenedione, 10-[(3-amino-2,3,6-trideoxy-α-L-lyxo-hexopyranosyl)oxy]-7,8,9,10-tetrahydro-6,8,11-trihydroxy-8-(hydroxylacetyl)-1-methoxy-, hydrochloride (8S-cis)-] is a cytotoxic anthracycline antibiotic isolated from cultures of *Streptomyces peucetius* var caesius (U.S. Pat. No. 3,590,028). Doxorubicin intercalates the base pairs of the DNA double helix, thus inhibiting nucleic acid synthesis, inhibiting topoisomerase II, and producing oxygen radicals. It is a red-orange, crystalline powder, which dissolves easily in water.

When doxorubicin is administered as a single agent, a recommended dose per cycle is 60-75 mg/m$^2$ every three weeks. The drug is generally given as a single dose per cycle; however, it is possible to give the drug dosage per cycle in divided administrations (e.g., day 1 through 3, or days 1 and 8). Administration of doxorubicin in a weekly regimen has been shown to be as effective as the tri-weekly schedule. The recommended weekly dosage is 10-20 mg/m$^2$. In combination chemotherapy, the recommended dose per three-week cycle is in the 30-60 mg/m$^2$ range.

The frequency of administration, dosage amounts, and the duration of treatment of each of the active agents may be determined depending on several factors, e.g., the overall health, size and weight of the patient, the severity of the disease, the patient's tolerance to the treatment, and the particular treatment regimen being administered. For example, duration of treatment with FTS or the combination of FTS and the chemotherapeutic agent may last a day, a week, a year, or until remission of the disease is achieved. Thus, relative timing of administration of these active agents is not critical (e.g., FTS may be administered before, during, and after treatment with the chemotherapeutic agent).

As used herein, the term "effective amount" refers to the dosage(s) of FTS alone or in combination with the chemotherapeutic agent that is effective for the treating, and thus includes dosage amounts that ameliorate symptom(s) of the disorder and its associated manifestations, diminish extent of disease, delay or slow disease progression, or achieve partial or complete remission or prolong survival. The average daily dose of FTS generally ranges from about 50 mg to about 2000 mg, and in some embodiments, ranges from about 200 mg to about 1200 mg. The average dose of paclitaxel according to its prescribed regimen generally ranges from about 10 mg to about 300 mg, and in some embodiments about 10 mg to about 200 mg. The average dose of docetaxel generally ranges from about 10 mg to about 130 mg, and in some embodiments about 10 mg to about 100 mg. The average dose of cisplatin generally ranges from about 10 mg to about 170 mg, and in some embodiments about 10 mg to about 120 mg. The average dose for carboplatin generally ranges from about 30 mg to about 620 mg, and in some embodiments about 30 mg to about 400 mg. The average dose of gemcitabine generally ranges from about 50 mg to about 1700 mg, and in some embodiments about 50 mg to about 1000 mg. The average dose of doxorubicin generally ranges from about 10 mg to about 130 mg, and in some embodiments about 10 mg to about 100 mg.

In some embodiments, FTS is administered on a daily basis, e.g., each in single once-a-day or divided doses, while the chemotherapeutic agent is administered in accordance with its approved dosing schedule. In some embodiments, both drugs may be administered at the same or at different times.

The methods of the present invention may be used for the treatment of cancer in mammals, particularly humans. The actives may be administered in accordance with standard methods. In preferred embodiments, FTS is administered orally. In an oral dosage form, the FTS is typically present in a range of about 50 mg to about 500 mg, and in some embodiments, from about 100 mg to about 300 mg.

In some embodiments, FTS may be administered by dosing orally on a daily basis for three weeks, followed by a one-week "off period", and repeating until remission is achieved. In another embodiment, FTS may be administered by dosing twice daily and continuing the treatment until remission is achieved. Parenteral administration may also be suitable.

In preferred embodiments, the chemotherapeutic agent, e.g., paclitaxel, docetaxel, cisplatin, carboplatin, gemcitabine, and doxorubicin, is administered intravenously. The agent is typically administered as a drip infusion into the vein through a cannula. Agents may also be given through a central line, which is inserted under the skin into a vein near the collarbone, or into a PICC line which is inserted into a vein in the crook of the arm.

In some embodiments, the administration of FTS with the chemotherapeutic agent may be cyclic and repeated until remission is achieved. For example, in one treatment regimen, FTS (200 mg) is administered twice daily for a period of three weeks followed by a one-week interval without FTS ("off period") while the chemotherapeutic agent, e.g. gemcitabine (Gemzar®), is administered once weekly (1500 mg) for a period of three weeks, followed by a one-week rest period. The treatment regimen is repeated as many times as needed, e.g., until remission is achieved. Under this regimen, gemcitabine and FTS are administered in three-week cycles (with increasing or decreasing dose amounts as needed) each separated by a one-week "off period". Dosage reduction with each cycle or within a cycle may be applied based upon the amount of toxicity experienced by the patient. Combination chemotherapy may also be administered in accordance with standard procedures while dosing with FTS.

In another embodiment, the treatment regimen may entail administration with oral FTS (e.g., a capsule or a tablet) continuously without interruption (i.e., without an "off period") and intravenous cisplatin as a daily infusion for five days every three to four weeks until remission is achieved. Dosing regimens for administering the chemotherapeutic agent or agents may be administered according to standard procedures or may be adjusted to meet the particular needs of the patient.

Oral compositions for FTS and its analogs for use in the present invention can be prepared by bringing the agent(s) into association with (e.g., mixing with) a pharmaceutically acceptable carrier. Suitable carriers are selected based in part on the mode of administration. Carriers are generally solid or liquid. In some cases, compositions may contain solid and liquid carriers. Compositions suitable for oral administration that contain the active are preferably in solid dosage forms such as tablets (e.g., including film-coated, sugar-coated, controlled or sustained release), capsules, e.g., hard gelatin capsules (including controlled or sustained release) and soft gelatin capsules, powders and granules. The compositions, however, may be contained in other carriers that enable administration to a patient in other oral forms, e.g., a liquid or gel. Regardless of the form, the composition is divided into individual or combined doses containing predetermined quantities of the active ingredient or ingredients.

Oral dosage forms may be prepared by mixing the active pharmaceutical ingredient or ingredients with one or more appropriate carriers (optionally with one or more other pharmaceutically acceptable additives or excipients), and then formulating the composition into the desired dosage form e.g., compressing the composition into a tablet or filling the composition into a capsule or a pouch. Typical carriers and excipients include bulking agents or diluents, binders, buffers or pH adjusting agents, disintegrants (including crosslinked and super disintegrants such as croscarmellose), glidants, and/or lubricants, including lactose, starch, mannitol, microcrystalline cellulose, ethylcellulose, sodium carboxymethylcellulose, hydroxypropylmethylcellulose, dibasic calcium phosphate, acacia, gelatin, stearic acid, magnesium stearate, corn oil, vegetable oils, and polyethylene glycols. Coating agents such as sugar, shellac, and synthetic polymers may be employed, as well as colorants and preservatives. See, *Remington's Pharmaceutical Sciences*, The Science and Practice of Pharmacy, 20th Edition, (2000).

Liquid form compositions include, for example, solutions, suspensions, emulsions, syrups, elixirs and pressurized compositions. The active ingredient or ingredients, for example, can be dissolved or suspended in a pharmaceutically acceptable liquid carrier such as water, an organic solvent (and mixtures thereof), and/or pharmaceutically acceptable oils or fats. Examples of liquid carriers for oral administration include water (particularly containing additives as above, e.g., cellulose derivatives, preferably in suspension in sodium carboxymethyl cellulose solution), alcohols (including monohydric alcohols (including monohydric alcohols and polyhydric alcohols, e.g., glycerin and non-toxic glycols) and their derivatives, and oils (e.g., fractionated coconut oil and arachis oil). The liquid composition can contain other suitable pharmaceutical additives such as solubilizers, emulsifiers, buffers, preservatives, sweeteners, flavoring agents, suspending agents, thickening agents, colorants, viscosity regulators, stabilizers or osmoregulators.

Carriers suitable for preparation of compositions for parenteral administration include Sterile Water for Injection, Bacteriostatic Water for Injection, Sodium Chloride Injection (0.45%, 0.9%), Dextrose Injection (2.5%, 5%, 10%), Lactated Ringer's Injection, and the like. Dispersions can also be prepared in glycerol, liquid polyethylene glycols and mixtures thereof, and in oils. Compositions may also contain tonicity agents (e.g., sodium chloride and mannitol), antioxidants (e.g., sodium bisulfite, sodium metabisulfite and ascorbic acid) and preservatives (e.g., benzyl alcohol, methyl paraben, propyl paraben and combinations of methyl and propyl parabens).

In order to fully illustrate the present invention and advantages thereof, the following specific examples/experiments are given, it being understood that the same is intended only as illustrative and in no way limitative.

EXAMPLE 1

Experimental Design

The purpose of these in vitro and in vivo experiments was to assess the ability of FTS, alone and in combination with a chemotherapeutic agent, to impact lung cancer cell integrity and survival. Here, the effects of the Ras inhibitor FTS on growth of non-small cell lung carcinoma (NSCLC) cell lines H-1299 [American Type Culture Collection ("ATCC"), CRL-5803), H23 (ATCC, CRL-5800, K-Ras mutation), HTB54 (ATCC, K-Ras mutation), A549 (ATCC, K-Ras mutation) and on the growth of lung squamous cell carcinoma cell line SK-MES-1 (ATCC, HTB-58) were examined. FTS on tumor cell growth in a nude mouse model was also examined. In addition, the combination of FTS and a chemotherapeutic agent on tumor cell growth inhibition was examined. The primary goal was to determine: (I) whether FTS induced cell-cycle arrest in A549 cells and also whether FTS induced growth inhibition in all five human lung cancer cell lines; (II) whether FTS altered cytoskeleton organization in A549 cells; (III) whether FTS inhibited active K-Ras-GTP and inhibited anchorage-independent growth of lung cancer cells in A549 cells; (IV) whether A549 cells were resistant to apoptosis after exposure to a chemotherapeutic agent in the presence of FTS; (V) whether FTS administered i.p. inhibited tumor growth in both A549 and HTB-58 (SK-MES-1) nude mouse models and whether oral FTS, alone, and in combination with a chemotherapeutic agent inhibited tumor growth in the A549 lung cancer cell nude mouse model; and (VI) whether increasing concentrations of FTS sensitized human NSCLC cell lines H1734 and H2030 (KRAS mutations) and H1975 and H3255 (EGFR mutations) to cell death.

The results of the first set of experiments (I) demonstrated that FTS induced cell cycle arrest in A549 cells. In addition, FTS caused dose-dependent inhibition in A549, HTB54, and H23 cell lines (which harbor activated K-Ras) and in H-1299 and HTB-58 (SK-MES-1) cell lines (neither of which harbors mutated Ras). Thus, FTS inhibited the growth of tumor cells even when the cells did not harbor mutated Ras genes. Results also indicated that the half-maximal inhibitory concentration ($IC_{50}$) of FTS ranged between 30 to 75 μm depending on the cell line.

The second set of experiments (II) revealed that A549 cells treated with FTS showed strong actin stress fibers and focal adhesions as compared with the control cells. Thus, FTS altered cytoskeleton organization and cell morphology in the A549 cell line.

In the third set of experiments (III), FTS inhibited the development of A549 human lung cancer cell colonies. Thus, FTS inhibited the anchorage-independent growth of A549 cells. In addition, FTS reduced the amount of K-Ras-GTP in a dose-dependent manner.

The results of the fourth set of experiments (IV) revealed that FTS increased sensitivity of A549 cells to cytotoxic drugs. Results showed that the combination of FTS and the chemotherapeutic agent demonstrated that the combined treatment with both drugs was more effective than treatment with either drug alone in A549 cells.

In the fifth set of experiments (V), i.p. administration of FTS inhibited tumor growth in A549 and HTB-58 (SK-MES-1) cell nude mouse models. Thus, FTS (i.p.) inhibited tumor growth as elicited by A549 and SK-MES-1 cells in vivo. In addition, oral administration of FTS inhibited tumor growth in the A549 lung cancer cell nude mouse model. Results also indicated that the combinations of FTS and gemcitabine (oral) were more effective than treatment with either drug alone.

The results of a sixth set of experiments showed that FTS at increasing concentrations sensitized human NSCLC cell lines H1734 and H2030 (KRAS mutations) and H1975 and H3255 (EGFR mutations) to cell death.

Materials and Methods
Cell Culture

FTS was provided by Concordia Pharmaceuticals, Inc. (Ft. Lauderdale, Fla.). All cell lines were obtained from American Type Culture Collection ("ATCC") (Manassas, Va.). A549 cells, non-small-cell lung carcinoma (CCL, ATCC) cells, were cultured in Kaighn's modification of Ham's F-12 medium containing 1.5 g/l sodium bicarbonate, 10% fetal calf serum (FCS), 100 U/ml penicillin, and 100 μg/ml streptomycin. HTB54 lung carcinoma cells were cultured in McCoy's 5A medium with 10% FCS, 100 U/ml penicillin, and 10 μg/ml streptomycin. HTB-58 (SK-MES-1, ATCC), a human lung squamous cell carcinoma cell line, was cultured in Eagle's minimum essential medium with 2 mM L-glutamine and Earle's BSS, 1.5 g/l sodium bicarbonate, 0.1 mM non-essential amino acids, 1 mM sodium pyruvate, 10% FCS, 100 U/ml penicillin, and 100 μg/ml streptomycin. H23 (NCI-H23, ATCC), a human non-small-cell lung adenocarcinoma cell line, was cultured in RPMI 1640 medium with 2 mM L-glutamine, 1.5 g/l sodium bicarbonate, 4.5 g/l glucose, 10 mM HEPES, 1 mM sodium pyruvate, 10% FCS, 100 U/ml penicillin, and 100 μg/ml streptomycin. H1299 (NCI-H1299, ATCC), a non-small-cell lung carcinoma cell line, was cultured in RPMI 1640 medium with 2 mM L-glutamine, 1.5 g/l sodium bicarbonate, 4.5 g/l glucose, 10 mM HEPES, 1 mM sodium pyruvate, 10% FCS, 100 U/ml penicillin, and 100 μg/ml streptomycin. The cells were plated in 24-well plates in 1 ml of medium at a density of 5000 cells/well (or 2500 cells/well, HTB54) and incubated at 37° C. in a humidified atmosphere of 95% air and 5% $CO_2$. Cells were treated with the indicated concentrations of FTS (Concordia Pharmaceuticals, Sunrise Fla.) or with 0.1% $Me_2SO_4$ (DMSO) (vehicle) 24 h after plating and were counted 5 days later. Dead cells were counted after addition of Hoechst 33258 dye (Sigma-Aldrich, St. Louis, Mo.); 1 μg/ml) to vehicle-treated control cultures or to cultures treated for 24 or 48 h with 75 μM FTS. Fluorescence images were collected 5 min after the dye was added.

In drug combination experiments, cells were grown for 2 days in the absence or in the presence of 40 μM FTS and were then treated for 4 h with gemcitabine (100 or 200 nM), cisplatin (50 or 100 nM), doxorubicin (50 or 100 nM), or paclitaxel (2.5 or 5 nM). Live cells were counted after a further 3 days of incubation with or without FTS. Experiments were performed twice in quadruplicate.

BrdU Incorporation into DNA

A549 cells were plated on glass cover slips ($1.2 \times 10^5$ cells/well in 6-well plates) and incubated for 24 h in medium containing 5% FCS. The cells were then incubated for 24 h with or without 75 μM FTS and then for 24 h with 5-bromo-2-deoxyuridine (BrdU) (Zymed BrdU labeling kit, 1:100 dilution). Cells were fixed with 4% paraformaldehyde, permeabilized with 0.2% Triton X-100 (BDH, Poole, UK), washed with PBS, blocked with TBS Tween (TBST; 50 mM Tris, pH 7.4, 100 mM NaCl, 0.1% Tween 20) containing 1% bovine serum albumin (BSA), treated sequentially with 2 N HCl and 0.1 M sodium borate pH 8.5, and then blocked with goat γ-globulin and washed with TBST-BSA (described above). The cells were then labeled successively with mouse anti-BrdU antibody (Ab) (Zymed kit; 1:50 dilution), biotinylated rabbit anti mouse IgG (5 μg/ml), and Cy3-streptavidin (1.5 μg/ml). Cells with BrdU-stained nuclei were counted under a fluorescence microscope.

FACS Analysis

A549 cells were plated ($9 \times 10^5$ cells) in 10-cm plates, incubated for 24 h in medium containing 5% FCS, and then incubated for 24 or 48 h with or without 75 μM FTS. The cells were collected, resuspended in PBS containing propidium iodide (50 μg/ml; Sigma) and 0.05% Triton X-100, and subjected to analysis by a fluorescence-activated cell sorter (FACSCalibur; Becton Dickinson, Los Angeles, Calif.).

Immunofluorescence and Confocal Microscopy

A549 cells were plated on glass cover slips ($2 \times 10^4$ cells/well in 6-well plates), incubated for 24 h in medium containing 5% FCS, and then incubated for 48 h with or without 75 μM FTS. The cells were fixed and permeabilized at room temperature by successive incubations with 3.7% formaldehyde (20 min) and 0.2% Triton X-100 in PBS (5 min), then washed for 5 min with UB buffer (150 mM NaCl, 10 mM Tris pH 7.6, and 0.2% sodium azide in PBS) and blocked with 2% BSA in UB (UBB, 5 min). The fixed cells were incubated successively with naïve goat IgG for 30 min (200 μg/ml, Jackson ImmunoResearch Laboratories, West Grove, Pa.), anti-vinculin Ab for 1 h (1:400, Sigma-Aldrich), goat anti-mouse Cy2-conjugated Ab for 1 h (1:200, Jackson), and rhodamine-labeled phalloidin for 1 h (1:1000, Sigma-Aldrich). Between each of the above steps the cells were washed for 30 min with UBB. Lastly, the cover slips were washed with UB, dried, and mounted onto the slides with Muviol. F-actin (red) and vinculin (green) were visualized with a Zeiss LSM 510 confocal microscope fitted with non-leaking green and red fluorescence filters. Co-localization was assessed using the co-localization function of the LSM 510 software.

Hoechst Staining Procedures

Hoechst 33258 dye, an ultraviolet light-excitable dye that demonstrates increased fluorescence when bound to the condensed chromatin of apoptotic cells, was used to quantify apoptotic cells in cell culture after FTS treatments. In tissue culture, cells were seeded at a density of $20 \times 10^4$ cells in 6-well plates for 24 h. Once cells had reached 70% confluence in normal FCS, the media was changed to low serum media (0.5% FCS for) and FTS was added. Control cells were treated with 0.1% DMSO. Hoechst solution was added to each well for 5-10 min and three pictures from each well were taken while using fluorescence microscopy.

Anchorage-Independent Colony Formation Assay in Soft Agar

Noble agar (2% and 0.6%; Difco, Detroit, Mich.) was prepared in water and autoclaved. The 2% agar was melted in a microwave oven, mixed 1:1 with medium (×2 Kaighn's modification of Ham's F-12 medium with 20% FCS, 100 U/ml penicillin, and 0.1 mg/ml streptomycin) and poured onto 96-well plates (50 μl per well) to provide the 1% base agar. The 0.6% agar (5 ml) was mixed with 5 ml of medium (×2), containing $8 \times 10^4$ A549 cells, and the mixture (50 μl) was plated on top of the base agar. The cells were incubated for 19 days at 37° C. with or without the indicated concentrations of FTS (6 wells for the control and for each treatment) and colonies were stained with MTT (1 mg/ml for 4 h). The colonies were then visualized by light microscopy, imaged, and counted using the ImagePro software.

Ras, Rac and Rho Pull-Down Assays and Immunoblotting Procedures

A549 cells were incubated for 24 or 48 h with or without FTS, as described above, and then lysed with lysis buffer as described in Haklai, R., Gana-Weisz, M., Elad, G., et al., Biochemistry 37:1306-14 (1998). The apparent amounts of K-Ras-GTP in 0.5 mg protein of total cell lysates were determined by the glutathione-S-transferase (GST)-RBD (Ras-binding domain of Raf) pull-down assay, as described in (Elad-Sfadia, G., Haklai, R., Ballan, E., Gabius, H. J., Kloog, Y., J Biol Chem 277:37169-75 (2002). The apparent amounts of Rac1-GTP and of RhoA-GTP, each in 2 mg protein of total cell lysates, were determined, respectively, by pull-down assays with GST-PBD (Rac1-binding domain of PAK1)-conjugated and GST-Rhotekin BD (Rho-binding domain of Rhotekin)-conjugated beads [Benard, V., Bohl, B. P., Bokoch, G. M, J Biol Chem 274:13198-204 (1999); Fiordalisi, J. J., Keller, P. J., Cox, A. D., Cancer Res 66:3153-61 (2006). The pulled-down GTPases were subjected to SDS-PAGE followed by immunoblotting with the appropriate antibodies: anti K-Ras (1:30; Calbiochem, La Jolla, Calif.), anti Rac-1 (1:2500; Santa Cruz Biotechnology, Santa Cruz, Calif.), or anti RhoA (1:700; Upstate Biotechnology, Lake Placid, N.Y.). Immunoblots were exposed to 1:2500 peroxidase-goat anti-mouse IgG. Levels of phospho-ERK and phospho-Akt were determined by immunoblotting [Haklai, R., Gana-Weisz, M., Elad, G., et al., supra.] using rabbit anti phospho-ERK1/2 Ab (Santa Cruz Biotechnology, Santa Cruz, Calif.) and rabbit anti phospho-Akt Ab (Cell Signaling, Beverly, Mass.). Protein bands were visualized by enhanced chemiluminescence and quantified by densitometry using ImageJ computer software (National institutes of Health, Bethesda, Md.).

Animal Studies

Nude mice (6 weeks old) were housed in barrier facilities on a 12-h light/dark cycle. Food and water were supplied ad libitum. On day zero, A549 or HTB-58 cells ($5 \times 10^6$ cells in 0.1 ml PBS) were implanted subcutaneously (s.c.) just above the right femoral joint. After 5 or 11 days the mice were separated randomly into control groups that had received only the vehicle and FTS-treated groups. Daily FTS treatments were administered either intraperitoneally (i.p.) or orally. Tumor volumes or weights were determined as described in Barkan, B., Starinsky, S., Friedman, E., Stein, R., Kloog, Y., Clin Cancer Res 12:5533-42 (2006). Gemcitabine treatment (36 mg/kg, i.p.) was administered every 4 days.

Results

I. FTS Inhibited the Growth of A549, H-1299, H23, HTB54, and HTB-58 (SK-MES-1) Human Lung Cancer Cells.

The tumor cell lines of the present study were originally derived from human lung epithelial cells and are representative of lung cancers and its associated manifestations. Here, we examined the impact of Ras inhibitor FTS on growth of non-small cell lung carcinoma cell lines A549 (K-Ras mutation), H23 (K-Ras mutation), and H-1299. We also examined the impact of FTS on the growth of HTB23 lung epidermoid carcinoma cell line and on lung squamous cell carcinoma cell line HTB-58 (SK-MES-1).

Figure 2:
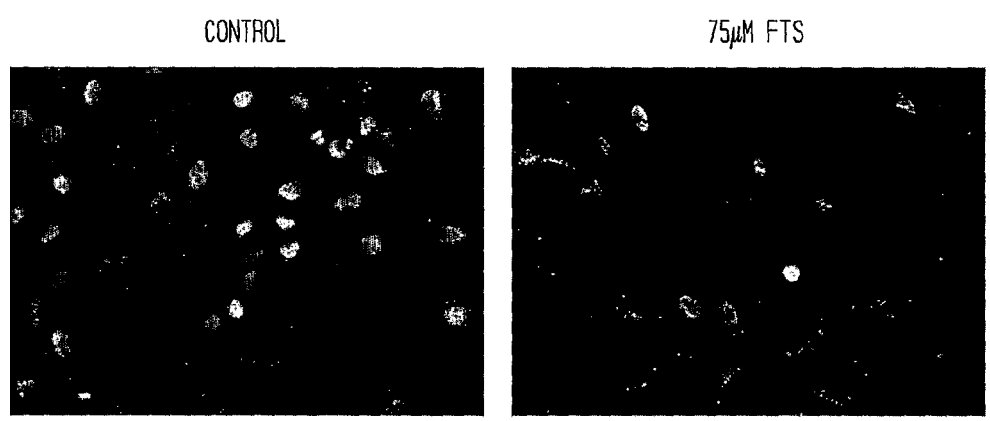
FIG. 2 are photomicrograph images of vehicle-treated (left) and FTS-treated (right) A549 cells (NSCLC) and further depicts the reduction in number of FTS-treated cells.
Figure 3:
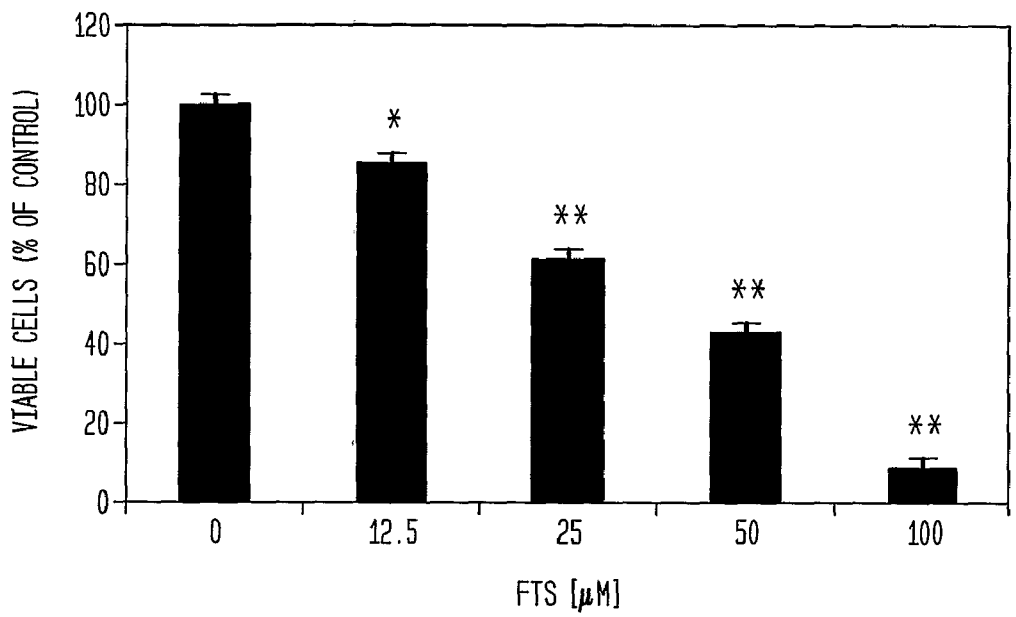
FIG. 3 is a bar graph illustrating the dose dependent inhibition of A549 cell (NSCLC) growth at increasing concentrations of FTS (µM), expressed as a percentage of control.
Figure 4:
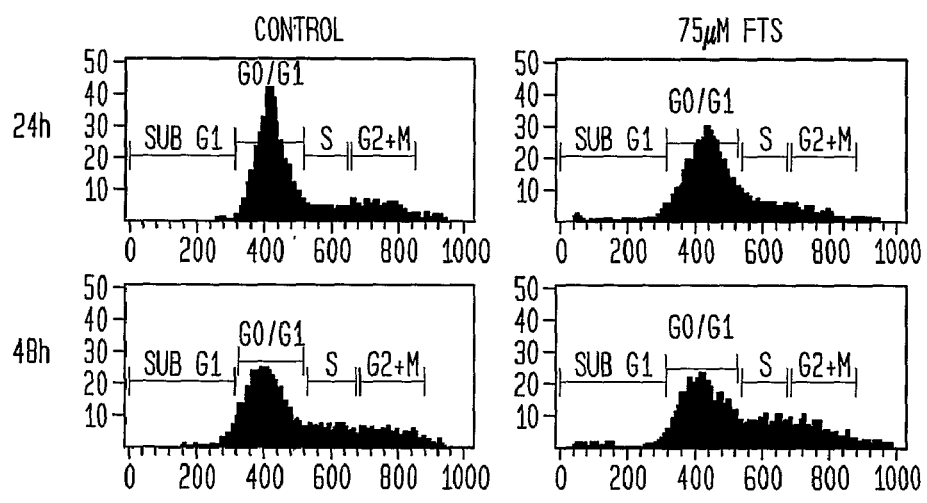
FIG. 4 illustrates the results of a FACS analysis describing FTS induced cell-cycle arrest in A549 cells (NSCLC).

To investigate the effect of FTS on lung cancer cell proliferation, we first incubated A549 cells that harbor the activated K-ras gene mutated at codon 12. A549 cells are commonly used as a model for drug screening. Incubation of the cells with 75 μM FTS for 48 h inhibited the incorporation of BrdU into their DNA by 56.7±17.4% relative to vehicle-treated control cells ($P<0.05$) (FIG. 1). Typical photomicrographs of control and 75 μM FTS-treated A549 cells (72 h) showed that FTS induced a reduction in cell number and altered the morphology of the cells (FIG. 2). Increasing concentration of FTS inhibited A549 cell growth at a dose dependent rate, with a decrease of 50% at 40 μM FTS. The number of cells in the FTS-treated cultures was determined by direct counting of A549 cells grown for 6 days in the presence of FTS and was expressed as a percentage of the number recorded in the controls. Data were means of 12 counts ±SD. *$P<0.01$, **$P<0.0005$, compared to control (FIG. 3). In another set of experiments, cells were also treated for 24 and 48 h with FTS and collected for FACS analysis (FIG. 4). The apoptotic population of cells (indicated in the FACS analysis as sub-G1) was 3.8% at 24 h and 8.4% at 48 h in cells treated with 75 μM FTS, compared to 1.0% and 2.8%, respectively, in control cells (FIG. 4). The results of these experiments also showed that FTS caused a reduction in the G1 population of cells but not in that of G2/M cells. Cells treated with FTS for 24 h and 48 h showed reductions in G1 of 5.6% and 19%, respectively (FIG. 3). Thus, FTS induced cell-cycle arrest in A549 cells, resulting in inhibition of cell growth.

Figure 5:
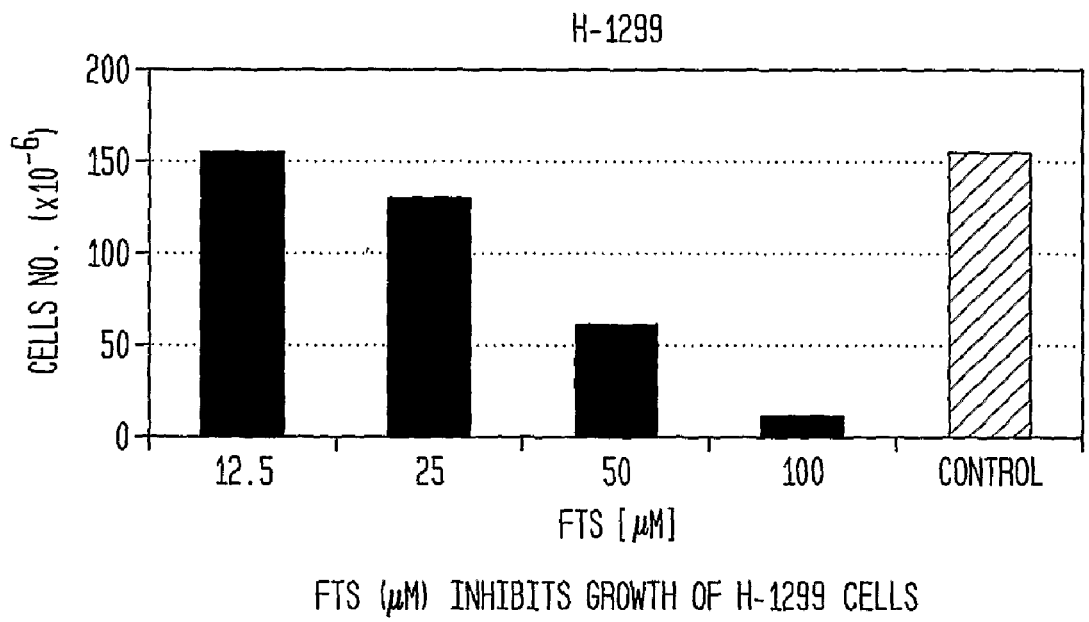
FIG. 5 is a bar graph illustrating the dose dependent inhibition of H-1299 cells (NSCLC) at increasing concentrations of FTS (µM) as determined by direct cell counting.
Figure 6:
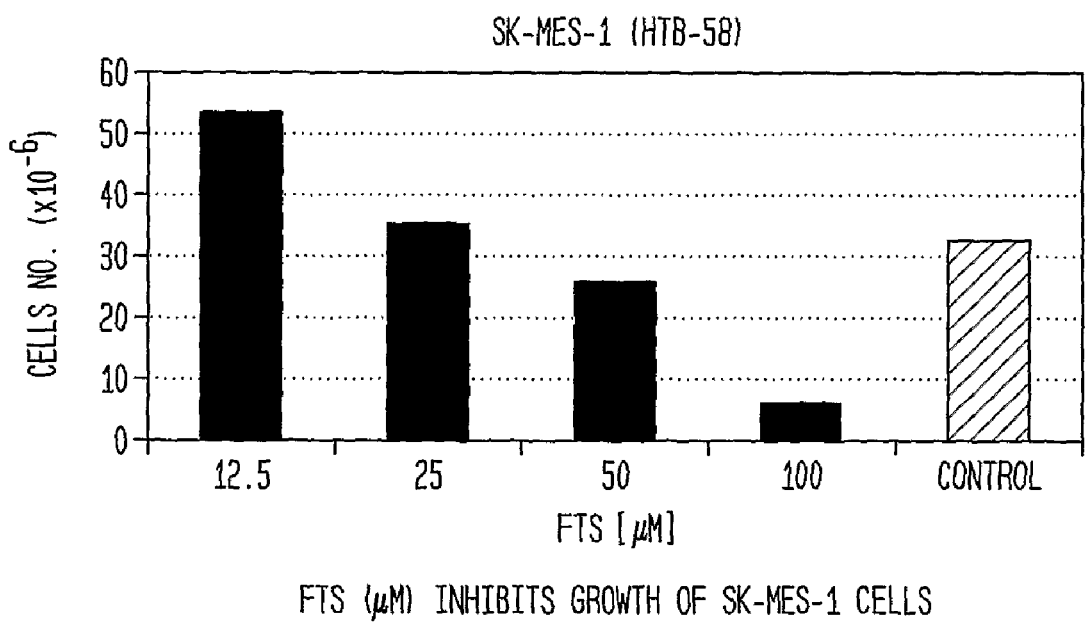
FIG. 6 is a bar graph illustrating the dose dependent inhibition of lung squamous cell carcinoma cell line HTB-58 (SK-MES-1) cells at increasing concentrations of FTS (µM) as determined by direct cell counting.
Figure 7:
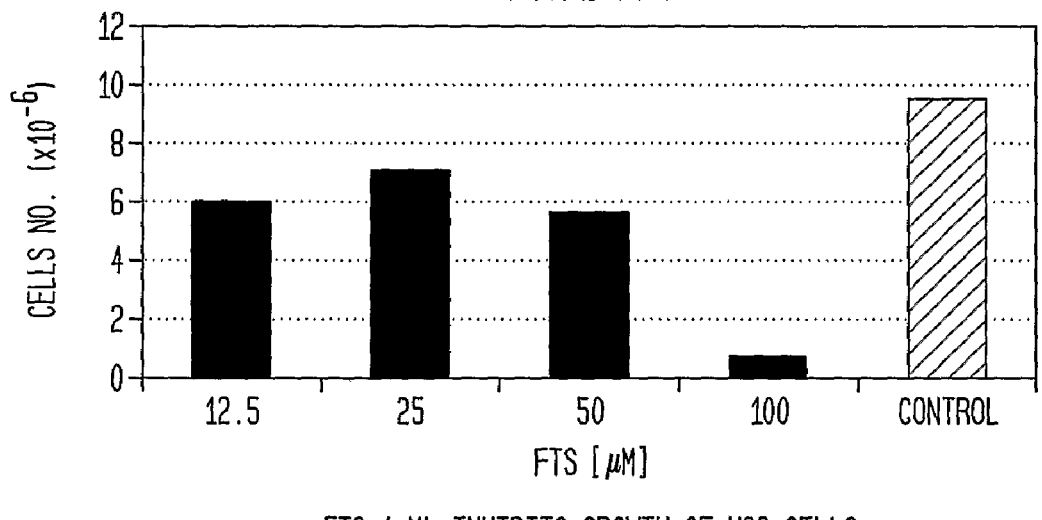
FIG. 7 is a bar graph illustrating the dose dependent inhibition of H23 cells (NSCLC) at increasing concentrations of FTS (µM) as determined by direct cell counting.
Figure 8:
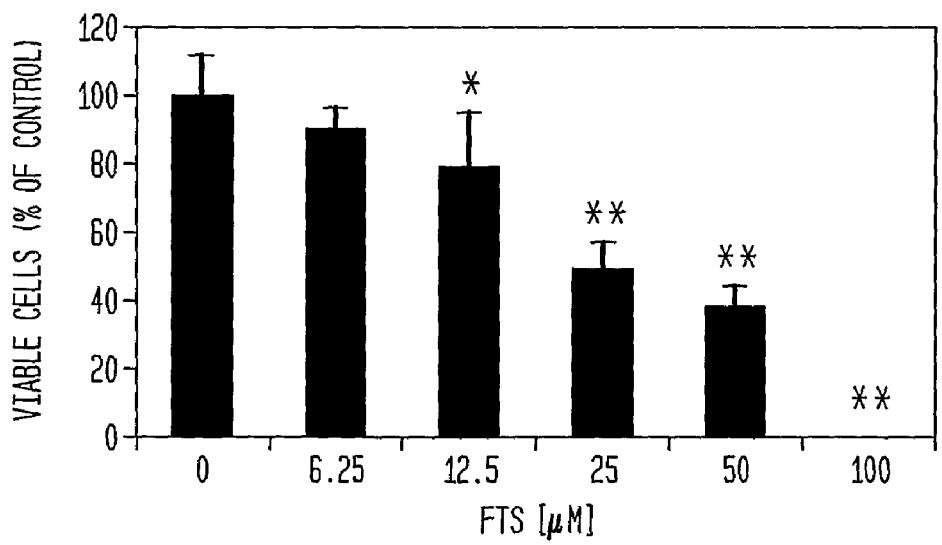
FIG. 8 is a bar graph illustrating the dose dependent inhibition of HTB54 lung epidermoid carcinoma cells at increasing concentrations of FTS (µM) as determined by direct cell counting.
Figures 9, 10:
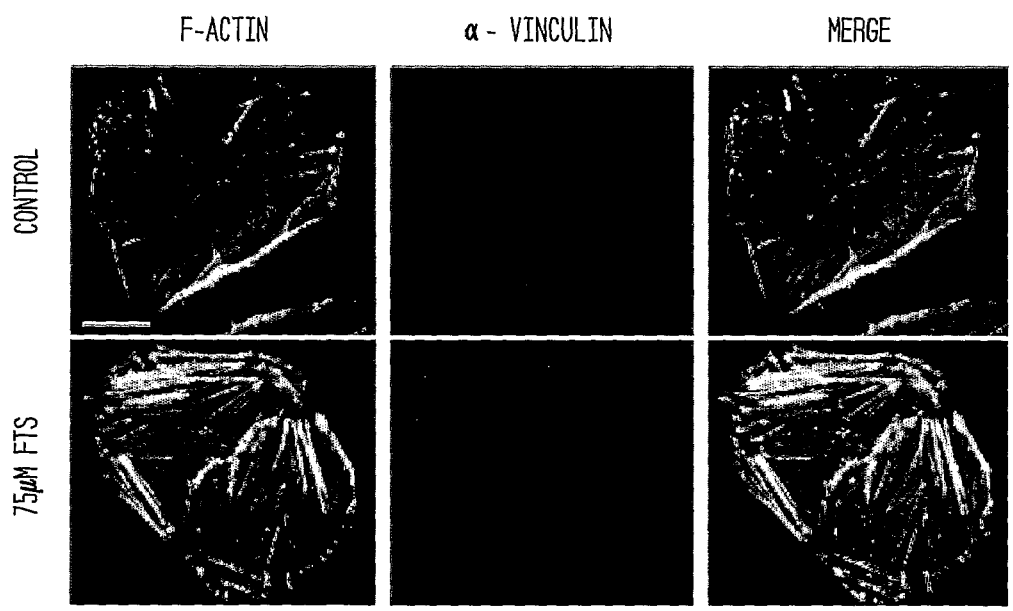
FIG. 9 is a table summarizing the half maximal inhibitory concentration ($IC_{50}$) of FTS (μM) in each of the human lung cancer cell lines [A549, H23, HTB54, H-1299, HTB-58 (SK-MES-1)].
FIG. 10 is a series of six fluorescent microscopic images illustrating FTS-induced alterations in stress fiber (F-Actin) and focal adhesion (α-Vinculin) formation on the cytoskeleton of A549 cells (NSCLC).

The growth-inhibitory effects of FTS were not limited to the A549 human lung cancer cells. Similar growth inhibition curves were obtained for H-1299 cells (FIG. 5) and SK-MES-1 cells (FIG. 6), which express relatively large amounts of EGF and insulin-like growth factor (IGF) receptors which activate Ras, and for H23 cells (FIG. 7) and HTB54 cells (FIG. 8), which harbor oncogenic K-Ras. The $IC_{50}$ values ranged between 30-75 μM FTS, depending on the cell line (FIG. 9).

II. FTS Altered Cytoskeleton Organization of A549 Cells.

Next, to determine the effects of FTS on the cytoskeleton of A549 cells, the cells were incubated, treated with 75 μM FTS, and stained with rhodamine-labeled phalloidin, which associates with polymeric F-actin, and with anti-vincullin, which associates with focal adhesions. Typical fluorescence images of control and of FTS-treated cells are shown in FIG. 10. Cells treated with FTS showed strong actin stress fibers and focal adhesions as compared with the control cells. The untreated cells exhibited short, thin actin stress fibers and relatively few focal adhesions, whereas the FTS-treated cells exhibited long, thick stress fibers and a relatively large number of focal adhesions that looked larger than those observed in the control cells. Statistical analysis indicated that more than 80% of the cells in the FTS-treated cultures had undergone changes in cell morphology. These results combined with the growth-inhibitory effects of FTS observed in lung cancer cell lines suggested that the FTS had, at least, partially reversed the transformed phenotype of the cells. Moreover, these results are consistent with the previous experiments that demonstrated an observed change in A549 cell morphology (FIG. 1).

III. FTS Inhibited Anchorage-Independent Growth of A549 Cells.

Figure 11A:
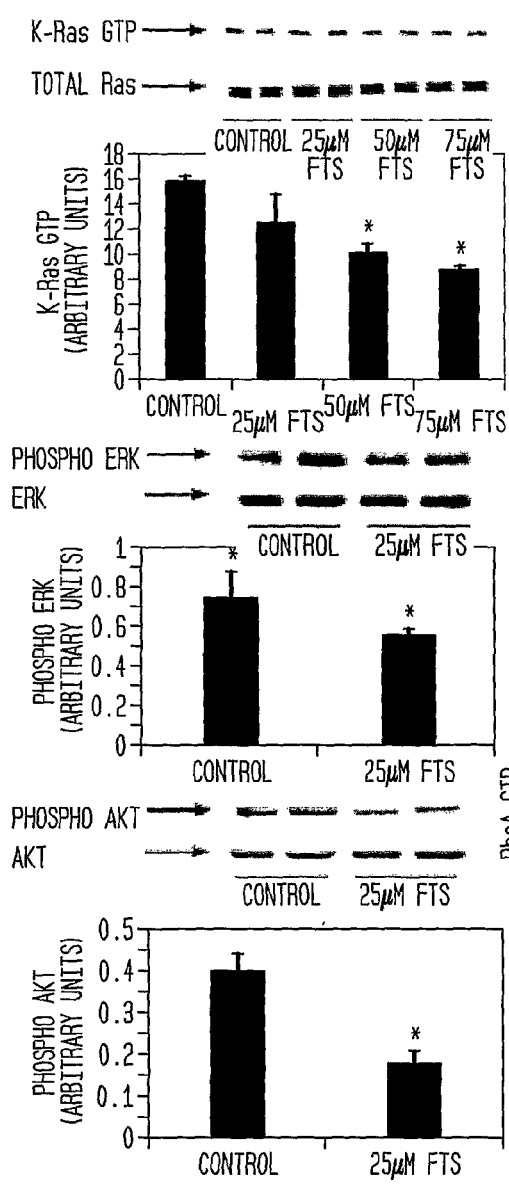
FIGS. 11A-11C are typical immunoblots and quantitative analyses of the results (means±SD of four experiments), as determined by densitometry and normalized to the level of expression of each protein. (A) illustrates the reduction in levels of K-Ras-GTP (upper panels) and of phospho-ERR and phospho-Akt (lower panels) by FTS. (B) illustrates the unaffected levels of Rac1-GTP by FTS. (C) illustrates the induced increase in RhoA-GTP by FTS (*$P<0.05$ compared to vehicle-treated control).

To determine whether active K-Ras-GTP and its prominent downstream signals to ERK and Akt were inhibited in A549 cells, and if so, whether the anchorage-dependent growth of the cells was also affected, two experiments were performed. First, A549 cells were incubated in the absence and in the presence of various concentrations of FTS and K-Ras-GTP, phospho-ERK and phospho-Akt levels were measured. FTS reduced the amount of K-Ras-GTP in a dose-dependent manner with no significant effect on the total amount of Ras (FIG. 11A). The reduction in K-Ras-GTP (mean±SD) was 23±15.3%, 37±3.7% (P<0.01), and 46±1.9% (P<0.002), respectively, in cells treated with 25 μM, 50 μM, and 75 μM FTS. The effective concentration range (50-75 μM) for the reduction in K-Ras-GTP (FIG. 11A) was similar to that required for the inhibition of cell growth (FIG. 3). FTS also reduced the levels of phospho-ERK and phospho-Akt causing 33±2% and 58±6% inhibition, respectively (FIG. 2).

Figure 11B:
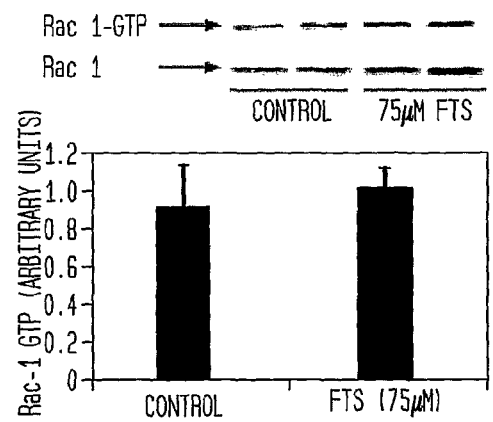
Figure 11C:
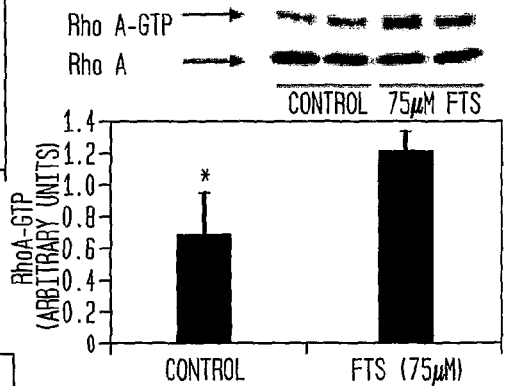

The effect of FTS appeared to be specific to the Ras protein, since it had no effect on the amount of the prenylated active Rac1-GTP protein as determined by a specific Rac1-GTP pull-down assay (FIG. 11B). Moreover, using a specific pull-down assay for prenylated active RhoA-GTP, FTS induced a significant increase of 2±0.2 fold (P<0.002) in RhoA-GTP (FIG. 11C). Thus, while FTS did not reduce the total amounts of the three GTPases (K-Ras, Rac-1, and RhoA), it clearly had a selective inhibitory effect on active K-Ras. The observed increase in RhoA-GTP is consistent with the observed increase in stress-fiber formation and focal adhesion assembly (FIG. 10).

Figure 12A:
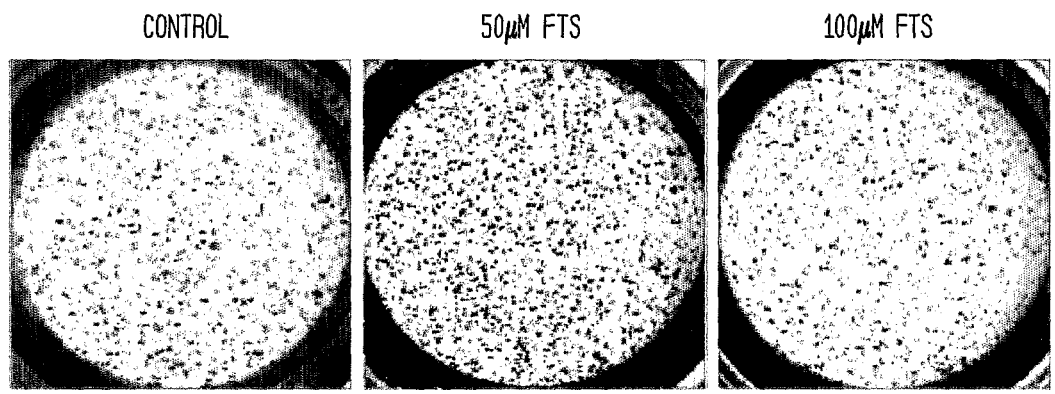
FIGS. 12A-12B illustrates the inhibition of the anchorage-independent growth or transformation of A549 cells (NSCLC) in soft agar by FTS. Photomicrograph images (A) illustrate the DMSO-treated (control) cells and colony formation before and after treatment with FTS (50 μM and 100 μM). The bar graph (B) illustrates the inhibition of A549 cell colony formation at increasing concentrations of FTS (0 μM, 50 μM, and 100 μM).
Figure 12B:
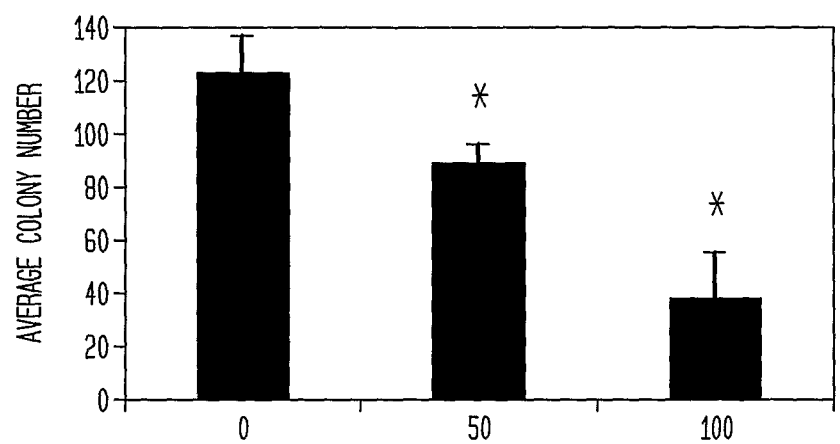

Next, to determine the effect of FTS on the anchorage-independent growth of A549 cells, a soft agar assay was performed. The cells were seeded in soft agar and treated with increasing concentrations of FTS 0 μM, 50 μM and 100 μM (FIGS. 12A-12B). Control cells were treated with 0.1% $Me_2SO_4$ (DMSO). FTS inhibited A549 cell growth in soft agar by 27±5.5% and 58±21% at 50 μM and 100 μM FTS, respectively. Thus, FTS inhibited the anchorage-independent growth of A549 cells.

IV. Combining FTS with a Chemotherapeutic Agent Enhanced Cell Death in Human Lung Cancer A549 Cells.

To determine whether A549 cells were resistant to apoptosis, an experiment to examine the survival of human lung cancer A549 cells after exposure to a chemotherapeutic agent in the presence of FTS was performed. Thus, to determine whether treatment with FTS can increase the sensitivity of A549 cells to cytotoxic drugs, A549 cells were incubated for 48 h with DMSO (control) or with 40 μM FTS, then for 4 h with gemcitabine, cisplatin, doxorubicin, or paclitaxel at the indicated concentrations. The cells were then washed and incubated for a further 72 h with DMSO or with 40 μM FTS. Live cells were collected and counted. The numbers of cells in the drug-treated cultures, expressed as percentages of the numbers in the vehicle-treated control, are shown in FIGS. 13A-13D. Values are means±SD. *P<0.05, **P<0.01, compared to vehicle-treated control.

Figure 13A:
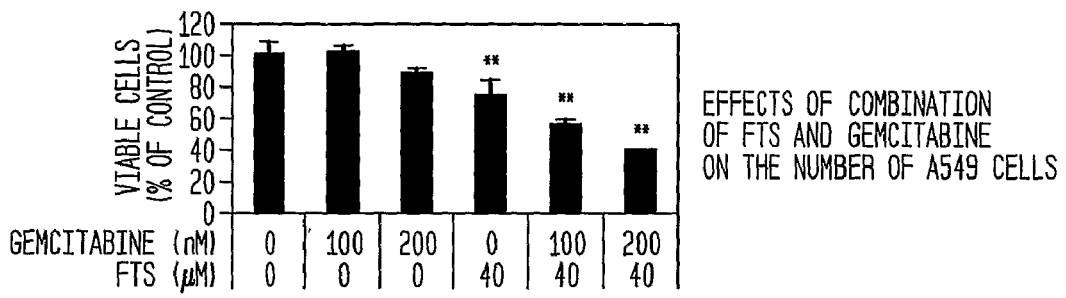
FIGS. 13A-13D are bar graphs illustrating (A) the effects of the combination of FTS (40 μM) and gemcitabine (0, 100, and 200 nM) on A549 cell (NSCLC) death; (B) the effects of the combination of FTS (40 μM) and doxorubicine (0, 50, and 100 nM) on A549 cell (NSCLC) death; (C) the effects of the combination of FTS (40 μM) and cisplatin (0, 5.0, and 10.0 nM) on A549 cell (NSCLC) death; (D) the effects of the combination of FTS (40 μM) and paclitaxel (0, 2.5, and 5.0) on A549 cell (NSCLC) death.
Figure 13B:
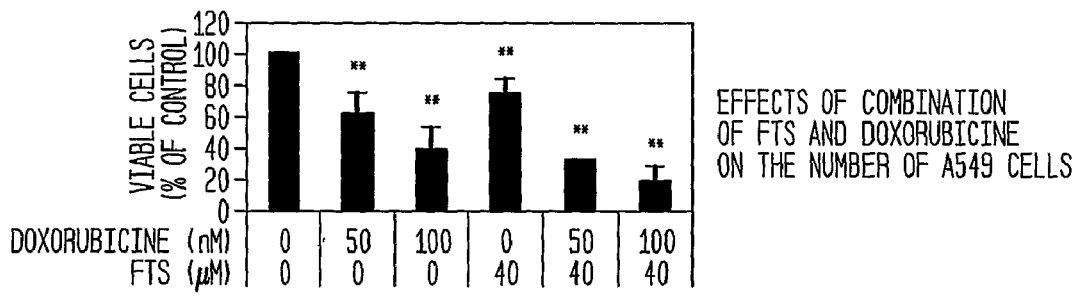

As shown in FIG. 13A, the effects of gemcitabine in the presence of FTS caused an enhanced increase in cell death that was measurably more effective than treatment with either drug alone in A549 cells. As shown, FTS alone caused a 25±6.3% reduction in cell numbers (mean±SD) at 40 μM, while gemcitabine alone at 100 and 200 nM had no effect (<11%). The combinations of FTS and gemcitabine at 100 and 200 nm enhanced cell number reductions of 45±5.3% and 60±5.7%, respectively.

Figure 13C:
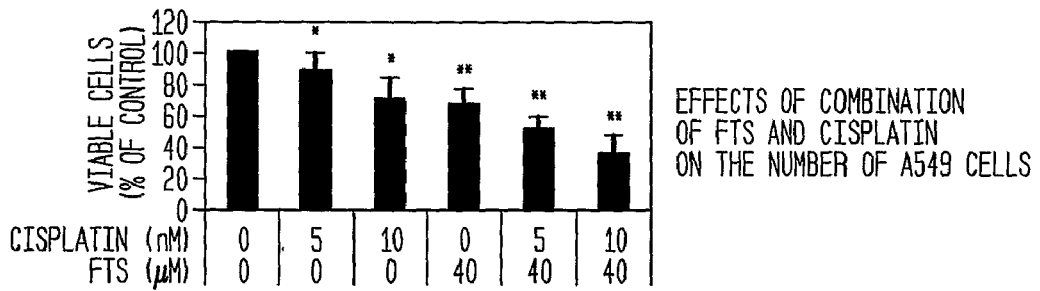
Figure 13D:
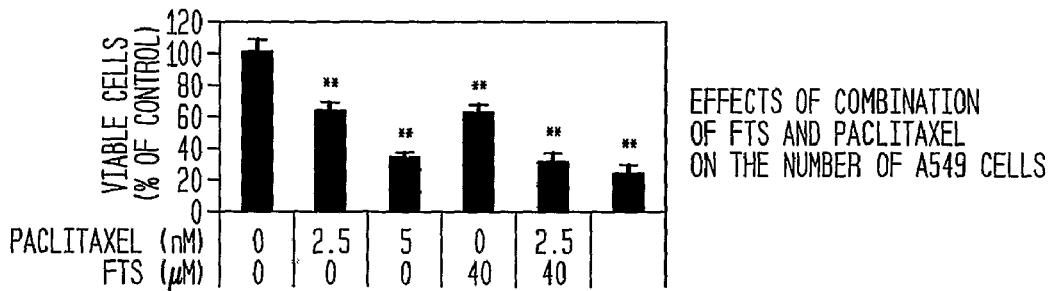

As shown in FIG. 13C, the effects of cisplatin in the presence of FTS caused an increase in cell death that was measurably more effective than treatment with either drug alone in A549 cells. As shown, FTS alone caused a 33±9.5% reduction in cell numbers (mean±SD) at 40 μM, while cisplatin alone at 50 and 100 nM caused reductions of 11±11% and 30±12.9%, respectively. The combinations of FTS and cisplatin at 50 and 100 nm caused cell number reductions of 47±6.9% and 63±12.7%, respectively.

As with cisplatin, the observed effects of the combinations of doxorubicin (FIG. 13B) and of paclitaxel (FIG. 13D) in the presence of FTS caused an increase in cell death that was measurably more effective than treatment with either drug alone in A549 cells.

V. FTS Alone and in Combination with a Chemotherapeutic Agent Inhibited Tumor Growth in Lung Cancer Cell Nude Mouse Models.

Figure 14A:
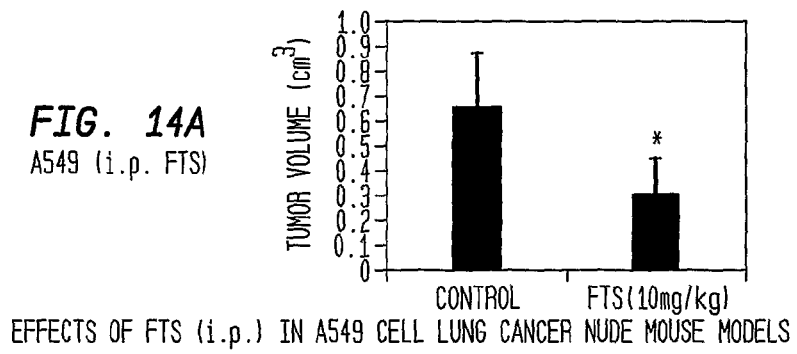
FIGS. 14A-14D are bar graphs illustrating (A) the effects of i.p. administration of FTS alone (10 mg/kg) in A549-cell-implanted nude mouse models; (B) the effects of i.p. administration of FTS alone (10 mg/kg) in HTB58-cell-implanted nude mouse models; (C) the effects of oral administration of FTS alone (50 mg/kg) in A549-cell-implanted nude mouse models; and (D) the effects of oral administration of FTS alone (60 mg/kg), the effects of oral administration of gemcitabine alone, and the combined effects of oral administration of FTS and gemcitabine in A549-cell-implanted nude mouse models.

To determine whether FTS inhibited tumor growth in vivo, experiments were conducted using a nude mouse model. The lung cancer cells were implanted s.c. above the right femoral joint and the mice were then treated with FTS. In a first experiment, the effect of i.p. administration of FTS on tumor growth in A549 cells was assessed. Treatment was started 5 days after cell implantation, by which time the tumors were palpable. Tumor volumes were determined 24 days after implantation in two groups of mice (n=8) that had received daily i.p. administration of either the vehicle (control) or 10 mg/kg FTS. Significant inhibition of tumor growth relative to the control (53.8%, P<0.05) was recorded in the FTS-treated group (FIG. 14A).

Figure 14B:
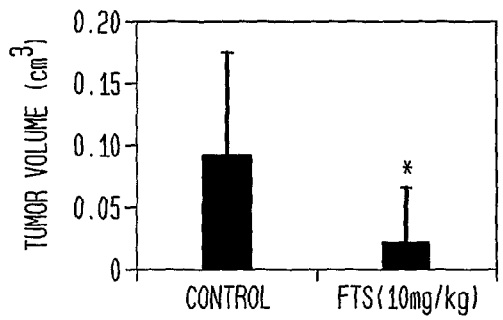

In a second experiment carried out with mice implanted s.c. with HTB-58 cells (n=7 per group), significant inhibition of tumor growth (76.4±48.8%) was observed in the group treated daily with 10 mg/kg FTS i.p. (FIG. 14B). Tumor volume measured 14 days after cell implantation in that group was 0.02±0.045 $cm^3$ compared to 0.09±0.08 $cm^3$ in the vehicle-treated controls (P<0.05).

Figure 14C:
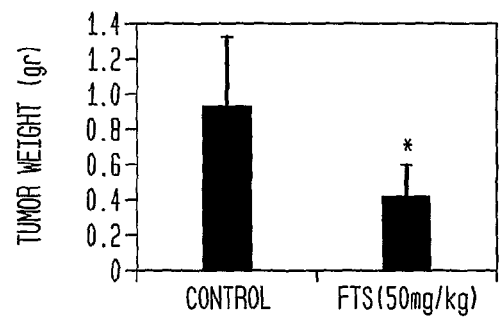
Figure 14D:
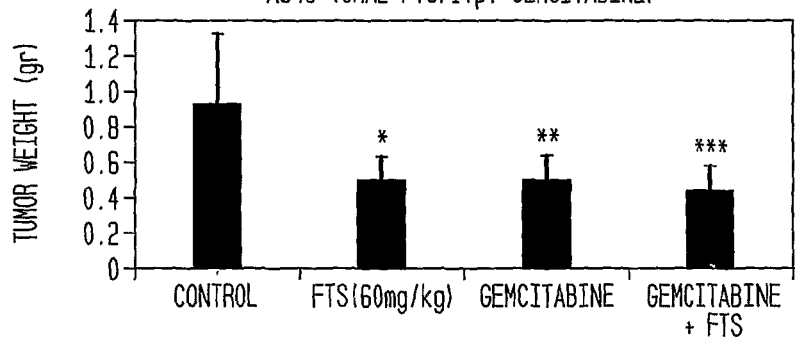

In an additional set of experiments, the A549-cell-implanted nude mouse model was used to examine the effect of orally administered FTS on tumor growth. First, cells were implanted as described above and daily oral treatment with FTS (50 mg/kg; n=6) or vehicle (n=5) was started either 11 days (FIG. 14C) or 6 days (FIG. 14D) after implantation. As shown in FIG. 14C, after 16 days of treatment the tumor weights (mean±SD) in FTS-treated and control mice were 0.4±0.19 g and 0.9±0.39 g, respectively, representing a significant inhibition of 53.7±19.1% in tumor growth (P<0.025) in the FTS-treated mice. Next, the effects of orally administered FTS, alone or in combination with gemcitabine, on A549-cell tumor growth was examined (FIG. 14D). Six days after cell implantation, mice were divided into four groups (n=8 per group) and treated orally with vehicle alone (control), FTS alone (60 mg/kg), vehicle and gemcitabine (36 mg/kg, i.p. every 4 days), or FTS and gemcitabine. Treatments with gemcitabine began 1 week after FTS treatment was started. Consistent with the results of the first experiment (FIG. 14C), oral FTS treatment caused a significant inhibition in tumor growth; tumor weights in the mice treated with vehicle only (control) and with FTS only (mean±SD) were 0.90±0.40 g and 0.49±0.15 g, respectively (46.2±16.3% inhibition, P<0.02; FIG. 14D). A significant reduction in tumor weight (P<0.015) was also observed in a fifth group of mice treated with gemcitabine alone (FIG. 14D). The combined effect of gemcitabine and FTS treatments were more effective than the effect of each treatment alone. Thus, the result reinforces the results of the in vitro experiments indicating that combined treatment with the two drugs was more effective than treatment with either of the drugs alone.

VI. FTS Alone Sensitized Human NSCLC Cell Lines H1734, H2030, H1975, and H3255 to Cell Death.

To determine whether FTS sensitized other human NSCLC cell lines to cell death, experiments were conducted on cell lines H1734 and H2030 (KRAS mutations) and H1975 and H3255 (EGFR mutations). The four cell lines were grown in increasing concentrations of FTS (dissolved in DMSO). After 96 hours, viable cells were quantified using an Alamar blue assay. Results are the mean±standard error of three independent experiments, in which there were 3 replicates of each condition, as shown in FIG. 15.

The publications cited in the specification, patent publications and non-patent publications, are indicative of the level of skill of those skilled in the art to which this invention pertains. All of these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating a human afflicted with lung cancer, comprising administering to the human an effective amount of FTS or an analog thereof as represented by the formula:

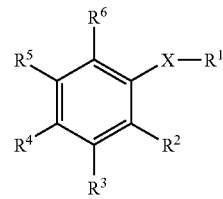

wherein
  $R^1$ represents farnesyl or geranyl-geranyl;
  $R^2$ represents the groups $COOR^7$, $CONR^7R^8$, wherein $R^7$ and $R^8$ are each independently hydrogen, alkyl or alkenyl, and COOM wherein
  M is a cation;
  $R^3$, $R^4$, $R^5$ and $R^6$ are each independently hydrogen, alkyl, alkenyl, alkoxy, halo, trifluoromethyl, trifluoromethoxy, or alkylmercapto; and
  X represents S; or a pharmaceutically acceptable salt thereof,
and
  a chemotherapeutic agent selected from the group consisting of gemcitabine.

2. The method of claim 1, wherein the human afflicted with lung cancer is administered FTS.

3. The method of claim 1, wherein FTS or its analog or a pharmaceutically acceptable salt thereof is administered orally.

4. The method of claim 1, wherein the chemotherapeutic agent is administered intravenously.

5. The method of claim 1, wherein the chemotherapeutic agent is gemcitabine.

* * * * *